(12) United States Patent
Goodchild et al.

(10) Patent No.: US 6,787,530 B1
(45) Date of Patent: *Sep. 7, 2004

(54) USE OF PREGNANE-DIONES AS ANALGESIC AGENTS

(75) Inventors: Colin Stanley Goodchild, Glen Waverley (AU); Raymond Nadeson, Prahran (AU)

(73) Assignee: Monash University, Malvern (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/197,161

(22) Filed: Nov. 20, 1998

Related U.S. Application Data

(63) Continuation-in-part of application No. 09/026,520, filed on Feb. 20, 1998, now Pat. No. 6,048,848, which is a continuation-in-part of application No. PCT/AU96/00531, filed on Aug. 23, 1996, now abandoned.

(51) Int. Cl.[7] .............................................. A61K 31/56
(52) U.S. Cl. ...................... 514/171; 177/179; 177/181
(58) Field of Search ................................. 514/171, 177, 514/179, 181; 552/176, 586, 589

(56) References Cited

U.S. PATENT DOCUMENTS

| | | | |
|---|---|---|---|
| 3,558,608 A | | 1/1971 | Klimstra |
| 3,781,435 A | | 12/1973 | Davis et al. |
| 3,822,297 A | | 7/1974 | Phillipps et al. |
| 3,917,830 A | | 11/1975 | Davis ........................ 424/243 |
| 3,943,124 A | * | 3/1976 | Phillipps et al. ....... 260/239.55 |
| 3,953,429 A | | 4/1976 | Cook ................. 260/239.55 R |
| 3,959,260 A | * | 5/1976 | Phillipps et al. ......... 260/239.5 |
| 4,045,574 A | | 8/1977 | Kerb .......................... 424/303 |
| 4,361,558 A | | 11/1982 | Wieland |
| 5,120,723 A | | 6/1992 | Gee ............................ 514/176 |
| 5,206,415 A | | 4/1993 | Covey ........................ 560/177 |
| 5,212,167 A | | 5/1993 | Farb ........................... 514/178 |
| 5,344,826 A | | 9/1994 | Covey ........................ 514/167 |
| 5,366,968 A | | 11/1994 | Farb ........................... 514/178 |
| 5,416,079 A | | 5/1995 | Campbell .................... 514/176 |
| 5,439,900 A | * | 8/1995 | Bukusoglu et al. ......... 524/177 |
| 5,550,120 A | | 8/1996 | Jackson ...................... 514/169 |
| 5,591,733 A | | 1/1997 | Bolger ........................ 514/172 |
| 5,593,983 A | | 1/1997 | Campbell .................... 514/176 |
| 5,763,431 A | | 6/1998 | Jackson ...................... 514/169 |
| 5,888,996 A | | 3/1999 | Farb ........................... 514/182 |
| 6,048,844 A | * | 4/2000 | Goodchild et al. ......... 514/171 |

FOREIGN PATENT DOCUMENTS

| | | | |
|---|---|---|---|
| AU | 36961/71 | 6/1973 | |
| DE | 2 162 554 | 6/1972 | |
| DE | 2 162 593 | 7/1972 | |
| DE | 2 255 108 | 8/1973 | |
| EP | 0348I911 | 1/1990 | ............. C07J/5/00 |
| FR | 2 318 646 | 2/1977 | |
| GB | 1 317 185 | 5/1973 | |
| WO | WO 93/04987 | 3/1993 | |
| WO | WO 9427608 | 12/1994 | .......... A61K/31/56 |
| WO | WO 9615782 | 5/1996 | .......... A61K/31/19 |
| WO | WO 9741867 | 11/1997 | ......... A61K/31/565 |
| WO | WO 9805337 | 2/1998 | .......... A61K/31/56 |

OTHER PUBLICATIONS

Parsons et al, On the selectivity of intravenous mu and kappa opioids, Br. J. Pharmacol.,98(2), 544–52, 1989.*
McIndewar,I.C., et al., *Interactions between the neuromuscular blocking drug Org NC45 and some anesthetic, analgesic and antimicrobial agents*, Br. J. Anaesth. vol. 53, No. 8, pp. 785–795 (1981). (abstract).
Nadeson, R. and Goodchild, C.S., *Alphaxalone/alphadolone a steroid anaesthetic combination (Saffan) produces antinociception at sub–anaesthetic doses: evidence for spinally–mediated antinociception by neuroactive steroids in rats*, in Proceedings of the Australasian Society of Clinical and Experimental Pharmacologists and Toxicologists (1994). (abstract).
Goodchild, C.S., et al., *Antinociception by intrathecal midazolam involves endogenous neurotransmitters acting at spinal cord delta opioid receptors*, Br. J. Anaesth. vol. 77, No. 6, pp. 758–763 (1996).(abstract).
Serrao, J.M., et al., *Intrathecal midazolam for the treatment of chronic mechanical low back pain: a conrolled comparison with epidural steroid in a pilot study*, Pain vol. 48, No. 1, pp. 5–12 (1992). (abstract).
Goodchild, C.S., et al., *Spinal cord effects of drugs used in anaesthesia*, Gen. Pharmacol. vol. 23, No. 6, pp. 937–944 (1992).(abstract).
Goodchild, C.S., et al., *The effects of intrathecal midazolam on sympathetic nervous system reflexes in man—a pilot study*, Br. J. Clin . Pharmacol. vol. 23, No. 3, pp. 279–285 (1987).
Goodchild, C.S., et al., *Intrathecal midazolam in the rat: evidence for spinally mediated analgesia*, Br. J. Anaesth. vol. 59, No. 12, pp. 1563–1570 (1987). (abstract).
Serrao, J.M., et al., *Intrathecal midazolam and fentanyl in the rat: evidence for different spinal antinociceptive effects*, Anesthesiol. vol. 70, No. 5, pp. 780–786 (1989).(abstract).
Goodchild, C.S., et al., *Analgesia mediated by spinal kappa–opioid receptors*, Eur. J. Anaesthesiol. vol. 8, No. 3, pp. 227–231 (1991).(abstract).

(List continued on next page.)

*Primary Examiner*—Alton Pryor
(74) *Attorney, Agent, or Firm*—Sterne, Kessler, Goldstein & Fox, P.L.L.C.

(57) ABSTRACT

A composition when used as an analgesic comprising a metabolite of a compound of Formula II wherein
$R^1$ is H or Me,
$R^2$ is OH,
$R^3$ is H;
or $R^2$ and $R^3$, taken together, are O;
$R^4$ is H or Me,
$R^5$ and $R^6$, taken together, are O;
$R^7$ is H or Me,
$R^8$=H, OH, OAc, SH, SAc, Cl, Br, F
together with a pharmaceutically acceptable diluent.

29 Claims, 9 Drawing Sheets

OTHER PUBLICATIONS

Goodchild, C.S. et al., *Antinociceptive actions of intrathecal xylazine: interactions with spinal cord opioid pathways*, Br. J. Anaesth. vol. 76, No. 4, pp. 544–551 (1996). (abstract).

Boulter, N., et al., *Spinally mediated antinociception following intrathecal chlordiazepoxide– further evidence for a benzodiazepine spinal analgesic effect*, Eur. J. Anaesthesiol., vol. 8, No. 5, pp. 407–411 (1991). ((abstract).

Edwards, M. et al., *On the mechanism by which midazolam causes spinally mediated analgesia*, Anesthesiol. vol. 73, No. 2, pp. 273–277 (1990). ((abstract).

Serrao, J.M. et al., *Reversal by Naloxone of spinal antinociceptive effects of fentanyl, ketocyclazocine and midazolam*, Eur. J. Anaesthesiol. vol. 8, No. 5, pp. 401–406 (1991). (abstract).

Nadeson, R., et al., *Gamma–aminobutyric acid A receptors and spinally mediated antinociception in rats*, J. Pharmacol. Exp. Ther. vol. 278, No. 2, pp. 620–626 (1996). (abstract).

Goodchild, C.S., et al., *Antinociception by intrathecal midazolam involves endogenous neurotransmitters acting at spinal cord delta opioid receptors*, Br. J. Anaesth. vol. 77, No. 6, pp. 758–763 (1996). (abstract).

Goodchild, C.S., et al., *5–HT spinal antinociception involved mu opioid receptors: cross tolerance and antagonist studies*, Br. J. Anaesth. vol. 78, No. 5, pp. 563–569 (1997). (abstract).

Nadeson, R., et al., *Antinociceptive properties of propofol: involvement of spinal gamma–aminobutyric acid(A) receptors*, J. Pharmacol. Exp. Ther. vol. 282, No. 3, pp. 1181–1186 (1997) (abstract).

Canavero, S., et al., *The neurochemistry of central pain: evidence from clinical studies, hypothesis and therapeutic implications*, Pain vol. 74, No. 2–3, pp. 109–114 (1998). (Abstract).

Sanchez–Valiente, S., [*Treatment of neuropathic pain with gabapentin + +*], Rev. Neurol. vol. 26, No. 152, pp. 618–620 (1998). (Abstract).

Deutsch, S.I., et al., *GABA–active steroids: endogenous modulators of GABA–gated chloride ion conductance*, Clin. Neuropharmacol. vol. 15, No. 5, pp. 352–364 (1992) (abstract).

Lin, Q., et al., *Glycine and GABAA antagonists reduce the inhibition of primate spinothalamic tract neurons produced by stimulation in periaqueductal gray*, Brain Res. vol. 654, No. 2, pp. 286–302 (1994). (abstract).

Smith, G.D., et al., *Increased sensitivity to the antinociceptive activity of (+/–)–baclofen in an animal model of chronic neuropathic, but not chronic inflammatory hyperalgesia*, Neuropharmacol. vol. 33, No. 9, pp. 1103–1108 (1994). (abstract).

Oliveras, J.L., et al., *The GABAA receptor antagonist picrotoxin induces a 'pain–like' behavior when administered into the thalamic reticular nucleus of the behaving rat: a possible model for 'central' pain?* Neurosci. Lett. vol. 179, No. 1–2, pp. 21–24 (1994). (Abstract).

Wang, R.A., et al., *Activation of mu–opioid receptor modulates GABAA receptor–mediated currents in isolated spinal dorsal horn neurons*, Neurosci. Lett. vol. 180, No. 2, pp. 109–113 (1994). (abstract).

Fromm, G.H., *Baclofen as an adjuvant analgesic*, J. Pain Symptom Manage. vol. 9, No. 8, pp. 500–509 (1994). (abstract).

Heinricher, M.M. et al., *Interference with GABA transmission in the rostral ventromedial medulla: disinhibition of off–cells as a central mechanisms in nociceptive modulation*, Neurosci. vol., 63, No. 2, pp. 533–546 (1994). (abstract).

Sear, J.W., et al., *Metabolism of alphaxalone in the rat: evidence for the limitation of the anaesthetic effect by the rate of degradation through the hepatic mixed function oxygenase system*, Br. J. Anaesth. vol. 53, No. 4, pp. 417–424 (1981). (abstract).

Holly, J.M., et al., *The in vivo metabolism of althesin (alphaxalone + alphadolone acetate) in man*, J. Pharm. Pharmacol. vol. 33, No. 7, pp. 427–433 (1981). (Abstract).

Craig, J., et al., *Recovery from day–case anaesthesia. Comparison between methohexitone, Althesin and etomidate*, Br. J. Anaesth. vol. 54, No. 4, pp. 447–451 (1982). (Abstract).

Olsen, R.W., et al., *Neuroactive steroid modulation of GABAA receptors*, Adv. Biochem. Psychopharmacol. vol. 48, pp. 57–74 (1995). (Abstract).

Stamford, J.A., *Descending control of pain*, Br. J. Anaesth. vol. 75, No. 2, pp. 217–227 (1995). (abstract).

Gordon, N.C., et al., *Enhancement of morphine analgesia by the GABAB agonist baclofen*, Neurosci. vol. 69, No. 2, pp. 345–349 (1995). (abstract).

Gilron, I. Et al., *Preemptive analgesic effects of steroid anesthesia with alphaxalone in the rat formalin test. Evidence for differential GABA(A) Receptor modulation in persistent nociception*, Anesthesiol. vol. 84, No. 3, pp. 572–579 (1996). (abstract).

Malcangio, M., *GABA and its receptors in the spinal cord*, Trends Pharmacol. Sci. vol. 17, No. 12, pp. 457–462 (1996). (abstract).

Tatsuo, M.A., et al., *Hyperalgesic effect induced by barbiturates, midazolam and ethanol: pharmacological evidence for GABA–A receptor involvement*, Braz. Med. Biol. Res. vol. 30, No. 2, pp. 251–256 (1997). (abstract).

Anderson, A., et al., *Anesthetic activity of novel water-soluble 2 beta–morpholinyl steroids and their modulatory effects at GABAA receptors*, J. Med. Chem. vol. 40, No. 11, pp. 1668–1681 (1997). (abstract).

Feng, J.O., et al., *Propofol potentiates the depressant effect of alfentanil in isolated neonatal rat spinal cord and blocks naloxone–precipitated hyperresponsiveness*, Neurosci. Lett. vol. 229, No. 1, pp. 9–12 (1997). (Abstract).

Kaneko, M. et al., *Role of spinal gamma–aminobutyric acidA receptors in formalin–induced nociception in the rat*, J. Pharmacol. Exp. Ther. vol. 282, No. 2, pp. 928–938 (1997). (abstract).

Field, M.J., et al., *Gabapentin (neurontin) and S–(+)–3–isobutylgaba represent a novel class of selective antihyperalgesic agents*, Br. J. Pharmacol. vol. 121, No. 8, pp. 1513–1522 (1997). (Abstract).

Field, M.J., et al., *Evaluation of gabapentin and S–(+)–3–isobutylgaba in a rat model of postoperative pain*, J. Pharmacol. Exp. Ther. vol. 282, No. 3, pp. 1242–1246 (1997). (Abstract).

Kalyuzhny, A.E., *Relationship of mu–opioid and delta–opioid receptors to GABAergic neurons in the central nervous system, including antinociceptive brainstem circuits*, J. Comp. Neurol. vol. 392, No. 4, pp. 528 (1998). (abstract).

Yang, S., et al., *Different GABA–receptor types are involved in the 5–HT–induced antinociception at the spinal level: a behavioral study*, Life Sci. vol. 62, No. 11, pp. PL143–8 (1998). (abstract).

Hill–Venning, C., et al., *The anaesthetic action and modulation of GABAA receptor activity by the novel water-soluble aminosteroid Org* 20599, Neuropharmacol. vol. 35, No. 9–10, pp. 1209–1222 (1996). (abstract).

Rady, J.J. et al., *Spinal GABA receptors mediate brain delta opioid analgesia in Swiss Webster mice*, Pharmacol. Biochem. Behav. vol. 51, No. 4, pp. 655–659 (1995). (abstract).

Bukusoglu, C. et al., *Analgesia with anesthetic steroids and ethanol*, Anesth. Analg. vol. 77, No. 1, pp. 27–31 (1993). (abstract).

Parsons, C., et al., *On the selectivity of intravenous mu–and kappa–opioids between nociceptive and non–nociceptive relfexes in the spinalized rat*, Br. J. Pharmacol. vol. 98, pp. 544–551 (1989).

Kavaliers, M. et al., *Analgesic effects of the progesterone metabolite, 3–alpha–hydroxy–5–alpha–pregnan–20–one, and possible modes of action in mice*, Brain Res. vol. 415, pp. 393–3989 (1987).

Fink, G., et al., *Sex differences in response to alphaxalone anaesthesia may be oestrogen dependent*, Nature vol. 298, pp. 270–272 (1982).

Grant, K. A. et al., *Ethanol–like discriminative stimulus effects of the neurosteroid 3–alpha–hydroxy–5–alpha–pregnan–20–one in female Macaca fascicularis monkeys*, Psychopharmacol. vol. 124, pp. 340–346 (1996).

Winfree, C.J., et al., *Analgesic effects of intrathecally–administered 3–alpha–hydroxy–5–alpha–pregnan–20–one in a rat mechanical visceral pain model*, Life Sci. vol. 50, pp. 1007–1012 (1992).

Lin, Q., et al., *Role of GABA receptor subtypes in inhibition of primate spinothalamic tract neruons: difference between spinal and periaqueductal gray inhibition*, J. Neurophysiol. vol. 75, No. 1, pp. 109–121 (1996).

Ewen, A., et al., *Hyperalgesia during sedation: effects of barbiturates and propofol*, Can. J. Anaesth., vol. 42, No. 6, pp. 532–540 (1995). (abstract).

Brazilian Journal of Medical & Biological Research, 1997, by Tatsuo, et al, "Hyperalgesic effect induced by barbiturates, midazolam and ethanol: pharmacological evidence for GABA–A receptor involvement".

Canadian Journal of Anesthesia, 1995, by Ewen, et al., "Hyperalgesia during sedation: effects of barbiturates and propofol in the rat."

The Macmilian Press Ltd., 1989, by Parsons, et al, pp 544–551, "On the selectivity of intravenous $\mu$—and κ–opioids between nociceptive and non–nociceptive reflexes in the spinalized rat."

Carl, P., et al., "Pharmacokinetics and pharmacodynamics of eltanolone (pregnanolone), a new steroid intravenous anaesthetic, in humans," *Acta Anaesthesiol. Scand.* 38:734–741, Acta Anaesthesiologica Scandinavica (Oct. 1994).

Chemical Abstracts vol. 75, Abstract No. 64113v, American Chemical Society (1971).

Chemical Abstracts vol. 75, Abstract No. 64114w, American Chemical Society (1971).

Chemical Abstracts vol. 75, Abstract No. 20793n, American Chemical Society (1971).

Chemical Abstracts, vol. 77, Abstract No. 105627c, American Chemical Society (1972).

Chemical Abstracts vol. 77, Abstract No. 9285v, American Chemical Society (1972).

Chemical Abstracts vol. 78, Abstract No. 102034, American Chemical Society (1973).

Chemical Abstracts vol. 79, Abstract No. 115783f, American Chemical Society (1973).

Chemical Abstracts vol. 79, Abstract No. 66672h, American Chemical Society (1973).

Eriksson, H., et al., "Comparison of eltanolone and thiopental in anaesthesia for termination of pregnancy," *Acta Anaesthesiol. Scand.* 39:479–484, Acta Anaesthesiologica Scandinavica (May 1995).

International Preliminary Examination Report for International Application No. PCT/AU 96/00531, completed Jul. 23, 1997.

Selyne, H., "Correlations Between the Chemical Structure and the Pharmacological Actions of the Steroids," *Endocrinology* 30:437–453, Endocrine Society (1942).

Supplementary Partial European Search Report for European Application No. EP 96 92 7448, completed Dec. 12, 2000.

Dialog File 351, Accession No. 882078, Derwent WPI English language abstract for DE 2 162 554 (Document AL1).

Dialog File 351, Accession No. 882077, Derwent WPI English language abstract for DE 2 162 593 (Document AM1).

Dialog File 351, Accession No. 953652, Derwent WPI English language abstract for DE 2 255 108 (Document AP1).

Derwent WPI Acession No. 1977–31357Y, English language abstract for FR 2 318 646 (Document AL2).

* cited by examiner

FORMULA I

FORMULA II

FORMULA III

0 – NO RIGHTING REFLEX
1 – RIGHTING BUT NO SPONTANEOUS MOVEMENT
2 – SPONTANEOUS MOVEMENT – UNCOORDINATED
3 – FULL RECOVERY

USE OF PREGNANE-DIONES AS ANALGESIC AGENTS

This application is a continution-in-part of application Ser. No. 09/026,720, filed on Feb. 20, 1998 now U.S. Pat. No. 6,048,848 which in turn is a continuation-in-part of PCT Application No PCT/AU96/00531 filed on Aug. 23, 1996 now abandoned.

FIELD OF THE INVENTION

This invention relates to compounds and compositions.

In a particular instance, the present invention relate to analgesia, methods of analgesia and analgesic compositions.

SUMMARY OF THE INVENTION

The present invention provides:
the new use of compounds of Formula II as shown in the accompanying drawings wherein $R^1$ is H or Me, preferably H;
$R^2$ is OH, preferably in alpha conformation;
$R^3$ is H;
or $R^2$ and $R^3$, taken together, are O;
$R^4$ is H or Me, preferably Me and preferably in alpha conformation;
$R^5$ and $R^6$, taken together, are O;
$R^7$ is H or Me, preferably H;
$R^8$=H, OH, OAc, SH, SAc, Cl, Br, F including solvates thereof, pharmaceutically acceptable derivatives thereof, prodrugs thereof, tautomers thereof, isomers thereof, and metabolites thereof.

The present invention also provides a method of analgesia comprising administering an effective amount of a compound of Formula II, wherein $R^1$ is H or Me, preferably H;
$R^2$ is OH, preferably in alpha conformation;
$R^3$ is H;
or $R^2$ and $R^3$, taken together, are O;
$R^4$ is H or Me, preferably Me and preferably in alpha conformation;
$R^5$ and $R^6$, taken together, are O;
$R^7$ is H or Me, preferably H;
$R^8$=H, OH, OAc, SH, SAc, Cl, Br, F including solvates thereof, pharmaceutically acceptable derivatives thereof, prodrugs thereof, tautomers thereof, isomers thereof, and metabolites thereof.

The present invention also provides an analgesic composition comprising a compound of Formula II, wherein $R^1$ is H or Me, preferably H;
$R^2$ is OH, preferably in alpha conformation;
$R^3$ is H;
or $R^2$ and $R^3$, taken together, are O;
$R^4$ is H or Me, preferably Me and preferably in alpha conformation;
$R^5$ and $R^6$, taken together, are O;
$R^7$ is H or Me, preferably H;
$R^8$=H, OH, OAc, SH, SAc, Cl, Br, F including solvates thereof, pharmaceutically acceptable derivatives thereof, prodrugs thereof, tautomers thereof, isomers thereof, and metabolites, thereof We have found unexpectedly that metabolites and prodrugs of compounds of Formula II are also active as analgesic agents. Therefore the invention further comprises a composition when used as an analgesic comprising a metabolite or a prodrug of a compound of Formula II wherein $R^1$ is H or Me, preferably H;
$R^2$ is OH, preferably in the alpha conformation
$R^3$ is H
or $R^2$ and $R^3$, taken together, are O;
$R^4$ is H or Me and preferably in the alpha conformation
$R^5$ and $R^6$, taken together, are O;
$R^7$ is H or Me, preferably R;
$R^8$=H, OH, Oac, SH, SAc, Cl, Cr, F.

In a further aspect of the invention there is disclosed a method of analgesia comprising administering an effective amount of a metabolite or a prodrug of a compound of Formula II wherein $R^1$ is H or Me, preferably H;
$R^2$ is OH, preferably in the alpha conformation
$R^3$ is H
or $R^2$ and $R^3$, taken together, are O;
$R^4$ is H or Me and preferably in the alpha conformation
$R^5$ and $R^6$, taken together, are O;
$R^7$ is H or Me, preferably H;
$R^8$=H, OH, Oac, SH, SAc, Cl, Cr, F.

PREFERRED ASPECTS OF THE INVENTION

The compounds of the invention are related to pregnanedione which is shown in Formula I.

The following Patent Specifications describe some of the compounds and their method of preparation:

British Patent Specification No. 1,317,185 (Application No. 33162/72 filed May 16, 1973) to GLAXO;

German Patent Specification No. 2,255,108 (based on British Application No. 52465/71 filed Nov. 11, 1971) to GLAXO;

U.S. Pat. No. 3,558,608 (granted Jan. 27, 1971, filed Dec. 30, 1968) to SEARLE;

South African Patent Specification 70/03861 (filed Jan. 15, 1971 based on British Application filed Jun. 20, 1969) to GLAXO;

German Patent Specification No. 2,162,554 (filed Jun. 29, 1972, based on British Application No. 60,068/70 filed Dec. 17, 1970) to GEAXRO;

French Patent Specification No. 2,1187121 (filed Sep. 1, 1972, based on British Application 60,068/70 filed Dec. 17, 1970) to GLAXO and German Patent Specification No. 2,162,593 (filed Jul. 6, 1972, based on British Application No. 60,067/70 filed Dec. 17, 1970) to GLAXO.

The whole of the subject matter of those specifications together with items 105627c and 9285v of Chemical Abstracts, Vol. 77, 1972; 64113v, 64114w, 20793n of Chemical Abstract 5, Vol. 75, 1971; 115783f and 66672h of Chemical Abstracts Vol 79, 1973; and 1020345 of Chemical Abstracts Vol 78, 1973 is to be considered included and imported hereinto.

A preferred compound for use is 21-acetoxy-3alpha-hydroxy-5alpha-pregnane-11,20-dione which is of Formula III and which is commonly referred to as alphadolone acetate.

Further preferred compounds of the invention include metabolites of alphadolone acetate.

More preferably a compound for use in the invention is alphadolone glucuronide.

The compounds may be used individually or in mixtures with other compounds or metabolites/prodrugs of compounds of Formula II.

In addition, compounds and metabolites of Formula II may be used concurrently with other analgesic drugs such as opioids to potentiate or increase the analgesic effects of those drugs. Suitable opioids for this use include morphine.

The compounds for use in this invention may be provided free acid form or as a salt. It is preferred that the compounds are provided as either sulphate or methane sulphonate salts.

The compositions of this invention may be prepared for administration by various routes including intravenous, intramuscular, peritoneal and any other convenient route. However, the applicant has found that effective results are obtained when a compound of Formula II is administered into the intestines particularly intragastically, and in a particular instance via an oral route.

Accordingly, in a preferred aspect, the present invention provides a composition in a form suitable for oral administration.

That form may include tablet, capsule or lozenge or a liquid form.

It is preferred that the composition contains a surfactant and/or a solubility improver. One solubility improver is water-soluble polyoxyethylated castor oil.

A suitable surfactant is Cremophor EL.

A suitable dosage in a 70 kg human would be about a maximum of 2.00 grams of the compound of Formula II every 6 hours.

We have conducted further scientific trials (see Examples 2 to 5) which provides evidence indicating that metabolites of alphadolone produced in the liver are responsible for the pain relieving effect of alphadolone when given orally and intraperitoneally to rats and orally to man. We have therefore prepared the following detailed description of such further evidence which we have obtained from our experimental data shown in Examples 2 to 5.

Alphadolone has been marketed as an anaesthetic (Saffan; Althesin) formulated in combination with another neurosteroid called alphaxalone. It is generally accepted in the literature that both alphaxalone and alphadolone are intravenous anaesthetics, i.e. when they are given intravenously, they produce sedation and unconsciousness to a level sufficient for surgery. Since the basis of our claim for the analgesic properties of alphadolone is that it does not produce sedation and unconsciousness when given as described in the patent, we though it important to investigate whether alphadolone on its own does have anaesthetic properties. Such data, although alluded to in the literature, is not stated clearly with scientific evidence. Thus, we performed the experiments described in Example 2. Rats were given an intravenous injection of alphadolone. All of the rats became unconscious and surgically anaesthetised within 5 seconds of the intravenous injection. The dose given intravenously would be expected to achieve blood levels very similar to a blood level that might be achieved after intraperitoneal injection of the dose of alphadolone used for anaesthesia in combination with alphaxalone. Thus, it can be concluded that intravenous injection of alphadolone produces unconsciousness. However, alphadolone given by other routes does not produce unconsciousness (vide infra).

Experiments with orally administered alphadolone are shown in Example 3 where. We have given a range of doses of alphadolone intragatrically to rats. Given by this route, alphadolone caused no sedation, even at very large doses. However, when the drug was given by this route, powerful antinociception (pain relief) occurred and this was due to an action of the drug or perhaps a metabolite on spinal cord receptors for the neurotransmitter gamma-aminobutyric acid (GABA). These, along with the results of experiments with intraperitoneal injections of alphadolone (Example 4 vide infra) encompass the essence of our discovery and invention, ie. the administration of a drug by a non-spinal route which produces pain relief by a selective action on spinal cord systems. Thus, pain relief is produced without alteration of conscious level, an extremely important property for a drug to be used as a pain reliever. That the drug does not have sedative properties when given intragastrically whereas it does when given intravenously implies that the body somehow alters the drug when given by this route. When a drug is absorbed from the stomach and intestine, the molecule is first presented to the liver in the body. One of the many functions of the liver is to metbolise compounds coming from the intestine. This may well have happened to the absorbed alphadolone to produce a metabolite which caused the effect. Since these data are included in our original patent application, we would say that the involvement of metabolites is implicit within these results, However, these results are supported further by subsequent experiments.

Experiments with intrapentoneal injections of alphadolone are shown in Example 4. Intrapentoneal injections of Saffan, the anaesthetic combination of alphaxalone and alphadolone produces unconsciousness to the state of surgical anaesthesia and subsequent sedation. However, after the sedation has completely worn off, there is revealed an antinociceptive (analgesic or pain relieving) effect. The experiments described in this document show that all of the sedative and anaesthetic properties of Saffan are due to its alphaxalone content when this combination is given intraperitoncally whereas the subsequent antinociceptive effects are totally due to the alphadolone content. By that we mean, when a dose of alphaxcalone is given, which is the same as the dose of alphaxalone given when the Saffan injection is administered, the same amount of anaesthesia and sedation is produced by the alphaxalone when given alone as is achieved with the Saffan. However, when the same dose of alphadolone is given alone that was administered in combination with alphaxalone in the Saffan injection, no sedation at all was produced but all of the antinociceptive effect was seen. Again, these results support the observations with the oral administration of alphadolone, i.e. that this drug does not produce any sedation when given by a route, which first presents the drug after absorption to the liver. It is likely therefore, that presentation of the alphadolone molecule to the liver prior to absorption into the rest of the body, inactivates the anaesthetic properties and activates the pain relieving properties; further evidence suggesting the involvement of metabolism and metabolites.

The experiments from our laboratory are supported by observations by an independent body, PAN LABS. A sample of alphadolone used in the above experiments in rats in our laboratory was sent to a commercial drug-testing house, called PAN LABS. They gave the drug to a number of preparations to look for toxicity effects as well as pharmacological effect. In one toxicity test performed at PAN LABS, doses of up to 300 mg per kg of alphadolone was given to mice. It was found that that dose did not produce anaesthesia, but merely a slight decrease in grip strength—the ability of the animal to hang on to a rod tightly with its forepaws whilst being pulled away from the rod.

Thus all of the above suggest that alphadolone and it's acetate salt are anaesthetics when given intravenously.

However, when the drug is given by a route which first presents the drug to the liver after absorption prior to gaining access to the rest of the body, the drug is somehow modified to destroy its anaesthetic and sedative potency, but simultaneously to activate it's analgesic effects. These observations are supported by experiments in humans (Example 5).

Experiments in humans conducted in Example 5 reports a Phase I/II study of oral administration of alphadolone in humans. The first pet of the study was a dose escalation study to assess safety. Doses up to 500 mg administered orally to humans produced no sedation or disorientation whatsoever. However, antinociceptive properties were observed. Doses of 250 mg and 500 mg given orally simultaneously reduced the morphine requirement for pain relief after major knee surgery and at the same time improved the pain relief, i.e. greater pain relief was reported by these patients taking alphadolone whilst they were using less morphine. None of these doses of alphadolone produced overt sedation, thus showing the potential of this drug as an analgesic without altering conscious level. It also supports the notion of the usefulness of a combination of alphadolone with an opioid.

The patients who had alphadolone administered orally to them, had blood samples taken at time 0, the time of drug administration, and at ½ hour intervals for 6 hours This blood was sent off to a laboratory at the Royal Melbourne Institute of Technology for analysis of blood alphadolone levels. It can be seen from Example 5 that no measurable alphadolone was found in the blood of these patients who were reporting useful analgesia with decreased morphine requirements. However, when the blood was treated with an enzyme which removes the glucuronide moiety from molecules, there was revealed the presence of alphadolone. These experiments mean that very little or no free alphadolone was present in these patient's blood, but large quantities of alphadolone was present as the glucuronide metabolite. This evidence supports further our claim that the analgesic effects of alphadolone and alphadolone acetate given by oral and intraperitoneal routes involves activity of metabolites in general and the glucuronide in particular.

EXAMPLES

Example 1

Figure 1:
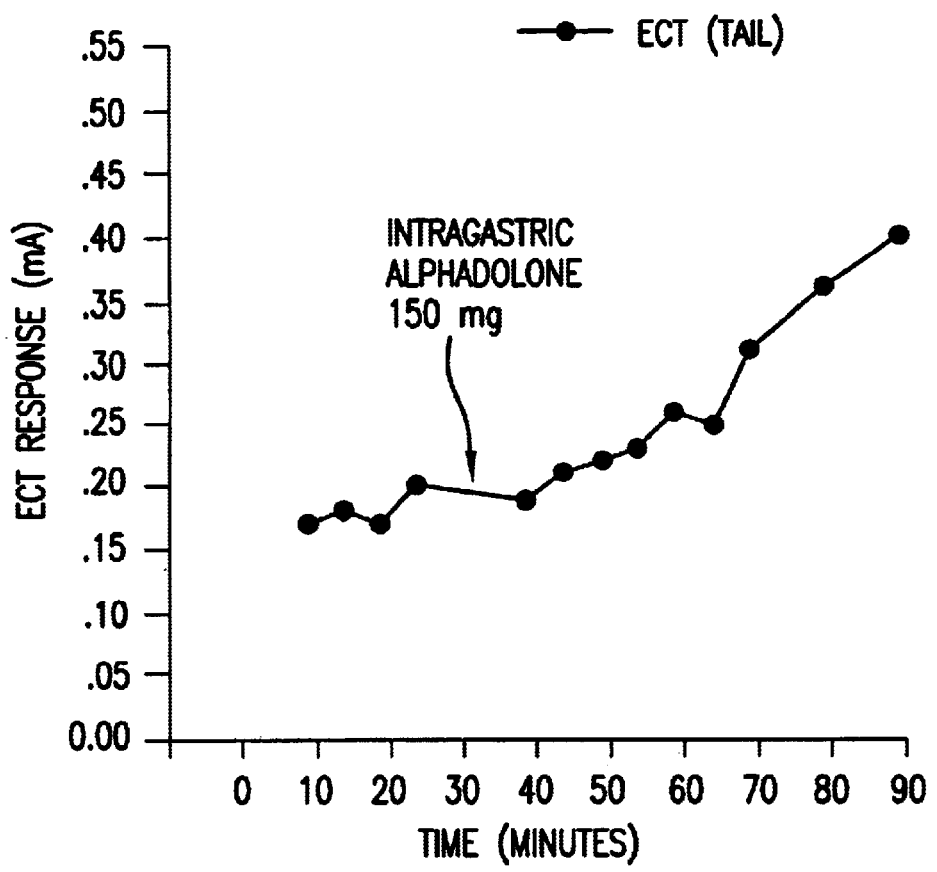
FIG. 1 is a graph showing results obtained.
Figure 2:
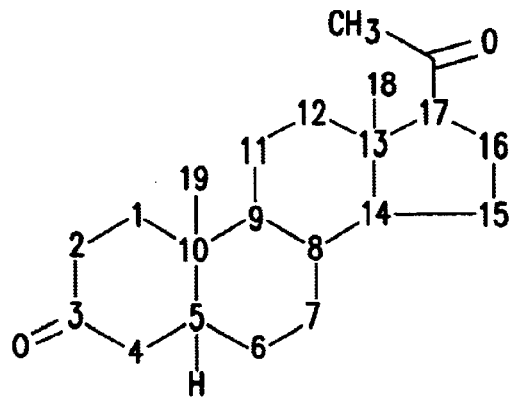
FIG. 2 is formula drawings.
Figure 2:
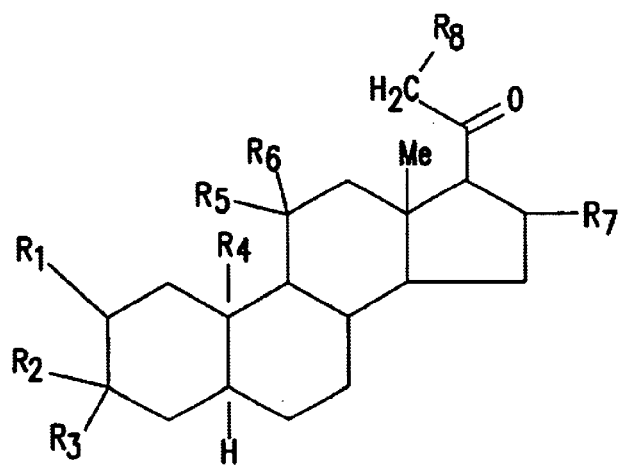
Figure 2:
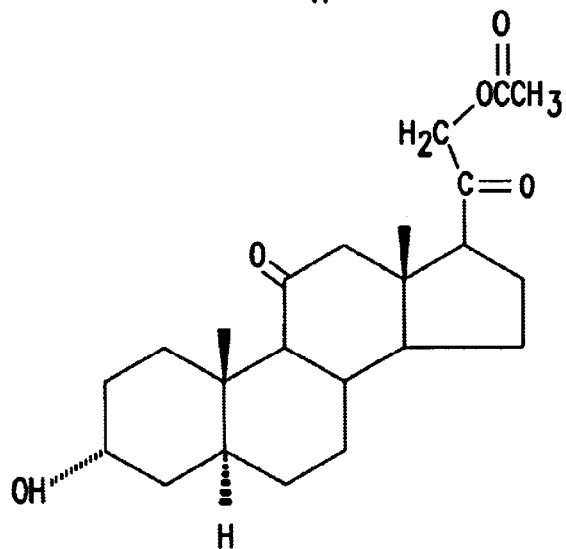

We performed a pilot experiment on one drug naive nale Wistar rat that weighed approximately 200 g. We measured the nociceptive (pain) threshold in the tail using electrical current as the noxious stimulus. We measured the electrical current threshold for pain (ECT) in the tail every five minutes until the readings stabilised. We then gave 150 mg alphadolone acetate suspended in 1% Cremophor EL, 99% saline, intragastrically. Subsequent ECT measurements as shown in FIG. 1 showed a significant rise in tail pain thresholds which lasted a long time after drug administration.

Example 2

Intravenous Alphadolone

Literature from Glaxo suggests that the alphadolone acetate component of Saffan is present in the mixture merely to improve the solubility of alphaxolone (the active ingredient) in the Cremophor EL. It is further reported from Glaxo in-house experiments that alphadolone is an intravenous anaesthetic like alphaxolone but one-third the potency. This information does not equate with our observations that doses of alphadolone up to 300 mg/kg given intraperitoneally caused no sedative effects whatsoever, an observation confirmed by the Pan Lab screen (see Example 5). The PAN Lab screen showed mild decrease in grip strength in mice after 300 mg/kg alphadolone.

It is quite clear however that the drug is absorbed in rats after IP and oral administration and in humans after oral administration because analgesic effects follow and metabolites can be shown in man (Example 5). One possible explanation is that glucuronidation or other metabolism occurs at the 21 position of the molecule that deactivates anaesthetic properties but preserves or imparts analgesic properties. Thus alphaxolone, which cannot be glucuronidated and is resistant to metabolism at the 21 position, is active as an anaesthetic when given IP as well as intravenously. However a drug injected IP or given orally is first presented to the liver; neurosteroids are known to have significant first pass metabolism at the liver. Thus alphadolone, which can be metabolised in general and specifically glucuronidated at the 21 position, appears in the general circulation as the glucuronide as we found in our human subjects (Example 5) or some other metabolite. There is the possibility that this metabolite is analgesic and not anaesthetic.

We do not know if Glaxo did their original tests with intravenous or IP injections. If the above theory is correct, they reported alphadolone to be an anaesthetic after intravenous injection. Since we have found alphadolone to be devoid of sedative/anaesthetic properties after IP injection we decided to investigate what happened after intravenous injection.

Four rats (wt 100 g) were given 0.25 ml injections of alphadolone solution (10 mg/ml; dissolved in 10% Cremophor EL), into the lateral tail vein. A stopwatch was used to time the following scoring of sedation every 15 seconds:

0—no righting reflex

1—righting reflex but no spontaneous locomotion

2—spontaneous locomotion but uncoordinated

3—normal locomotion and exploratory behaviour: full recovery

Figure 3:
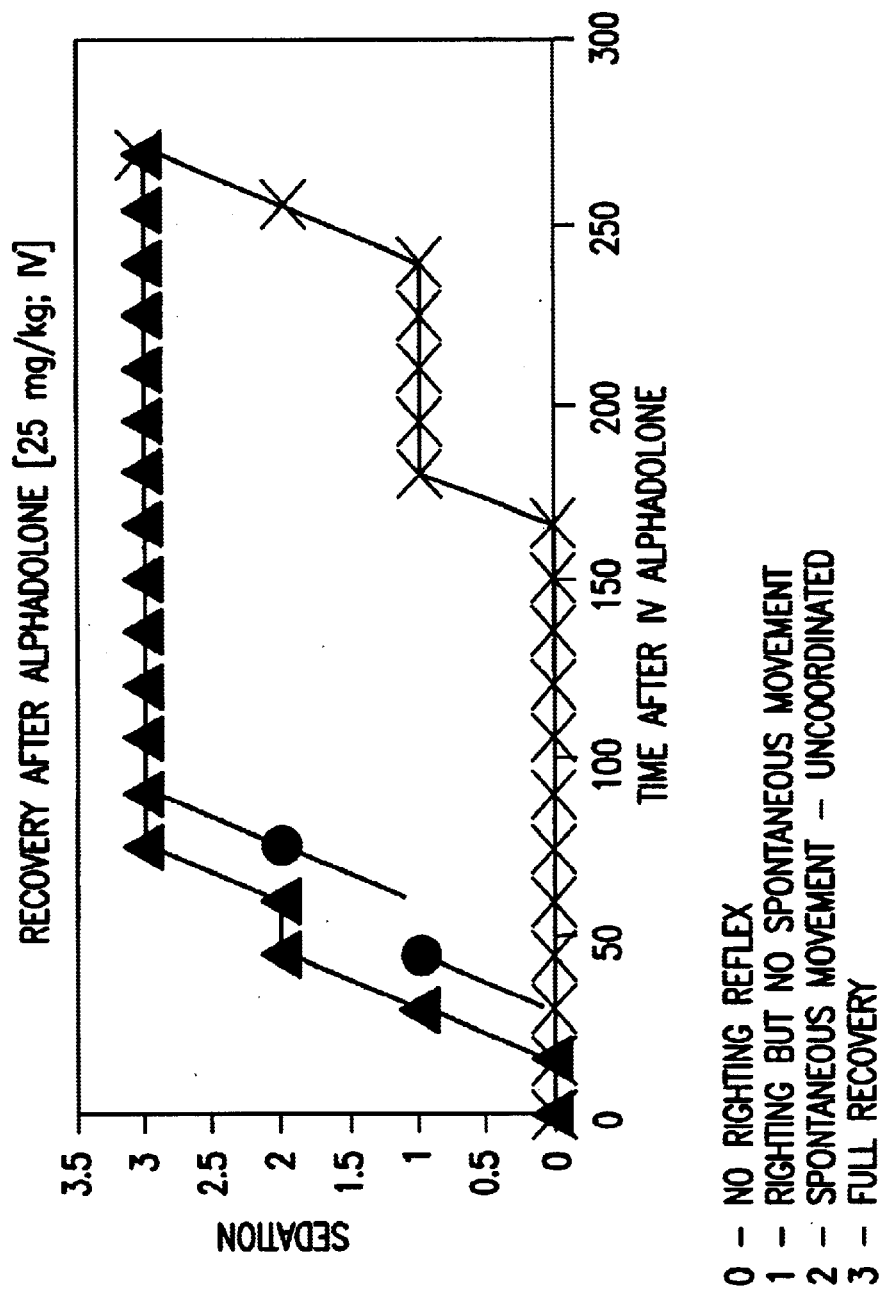
FIG. 3 is a graph showing results obtained.

All four rats lost the righting reflex and were heavily sedated after 25 mg/kg intravenous alphadolone acetate. They all recovered fully within 90 seconds of the drug administration. These results are shown FIG. 3.

We can conclude from these experiments with intravenous administration of alphadolone and others in which alphadolone was given intragastrically and intraperitoneally (IP) to rats and orally to humans (vide infra) that IP and oral administration of alphadolone inactivate the anaesthetic properties of alphadolone acetate. However the analgesic property is present after such administration and this is due to metabolites of alphadolone. Thus in this patent we wish to protect pro-drugs of alphadolone that would be metabolised in the body to produce alphadolone, which could then be metabolised in the body to produce the active metabolites described in our experiments. Furthermore we wish to cover the use of all such metabolites of alphadolone as analgesics given by whatever route of administration.

Example 3

Figure 4A:
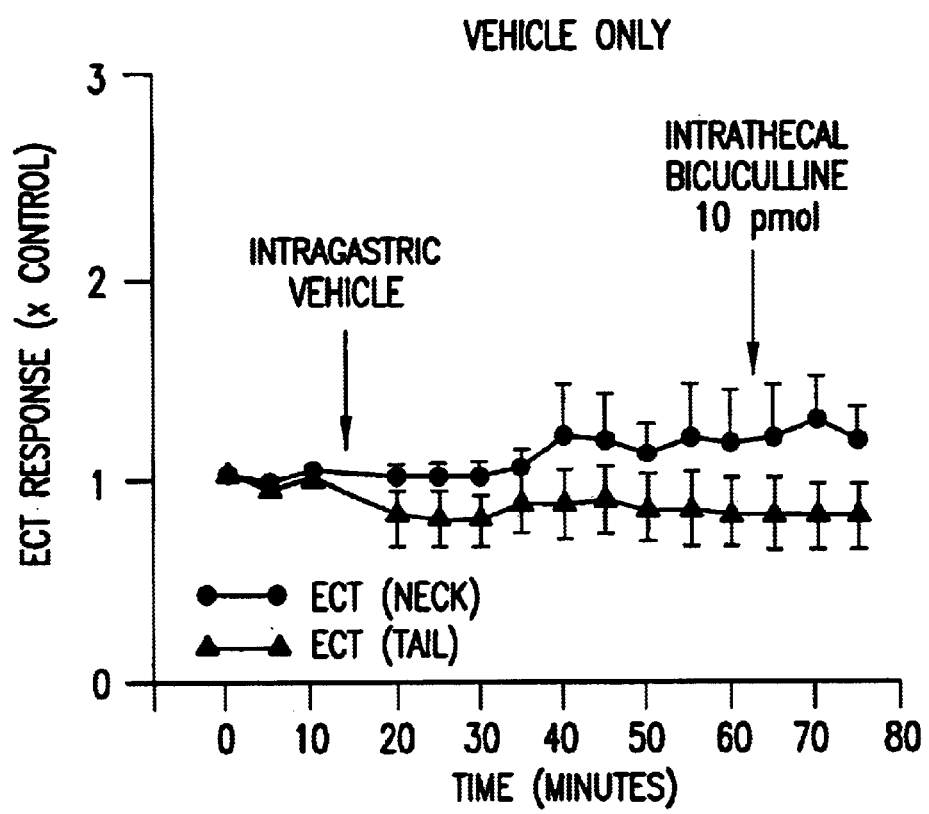
FIG. 4 is a graph showing results obtained.
Figure 4B:
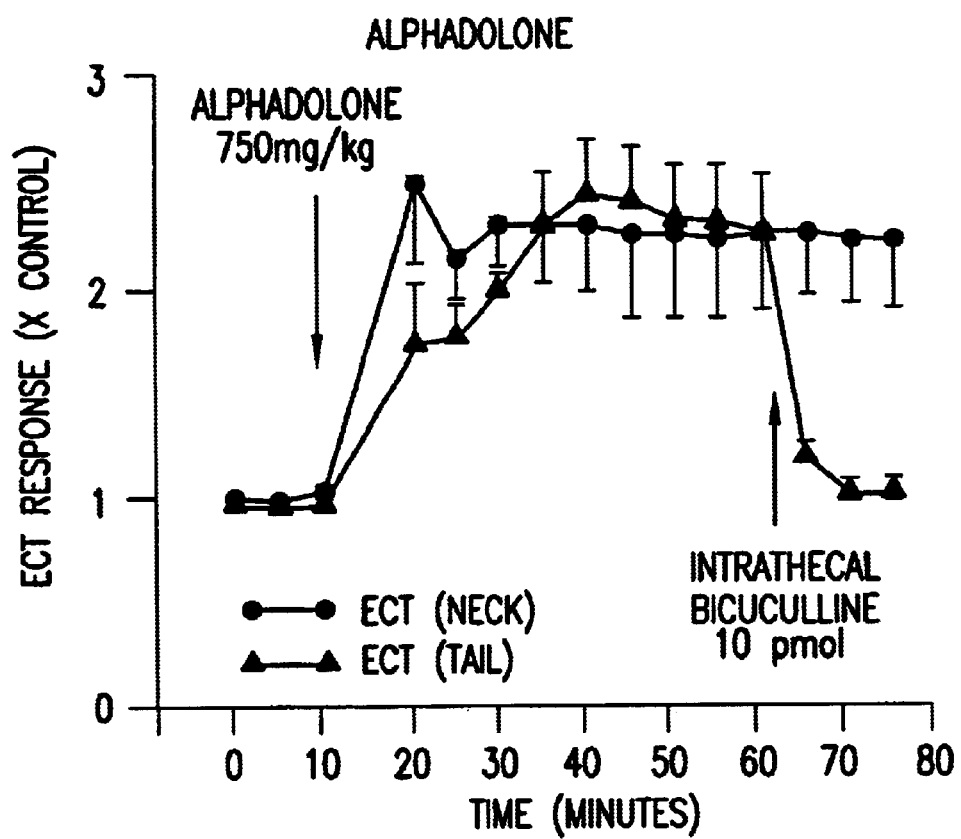

A study was performed on five rats. The results of this latter study are shown in FIG. 4. Alphadolone (750 mg/ml) was suspended in normal saline. The five rats were randomised to receive on two different occasions on two different days either intraperitoneal vehicle or intraperitoneal alphadolone. This was a cross-over study such that on the following occasion if a rat had received vehicle on the first occasion then it received alphadolone on the second occasion and vice versa. This dosing was randomised and the observer making measurements of pain thresholds was blinded to the nature of the drug given to these rats. In each experiment, the electrical current threshold in the neck and the tail were measured every five minutes until three stable readings were obtained. Then either vehicle or alphadolone 750 mg per kg suspended in saline was instilled into the stomach via an oesophageal needle. Five minutes later and every five minutes thereafter, electrical current thresholds for nociception were measured in the skin of the tail and neck At 60 minutes 10 pmol of bicuculline in 5 $\mu$l 6% dextrose was injected intrathecally down a Portex catheter that had been implanted previously in the lumbar sub arachnoid space to lie adjacent to the most caudal segments of spinal cord responsible for tail innervation. The rsults for tail and neck electrodes for each treatment (vehicle or alphadolone) were combined to produce time response curves which are shown in FIG. 4.

It can be seen that intragastric vehicle produced no antinociceptive effects in either the tail or neck electrodes. By contrast intragastric alphadolone 750 mg per kg produced a sharp rise in the electrical current threshold in the skin of the tail and the neck. Observation of the animals during this time revealed no differences by the groups with regard to sedation i.e. no animals seemed to be sedated in any form whatsoever. Intrathecal bicuculline produced no changes in the electrical current threshold in the tail or the neck in those experiments where intragastric vehicle had been administered. By contrast intrathecal bicuculline injection completely reversed the antinociceptive effects of oral alphadolone when measured in the tail with no change in the neck thresholds. These results indicate that injection of bicuculline onto the most caudal segments of the spinal cord only reversed the antinociceptive effects in the tail ie. the region of the body innervated by those most caudal segments of the spinal cord. Since bicuculline is a $GABA_A$ antagonist and since the neck threshold remained unchanged one may conclude that non-sedating doses of oral alphadolone produced long-lasting antinociceptive effects mediated by combination of the drug with spinal cord $GABA_A$ receptors even though the drug was given orally.

Example 4

Figure 5:
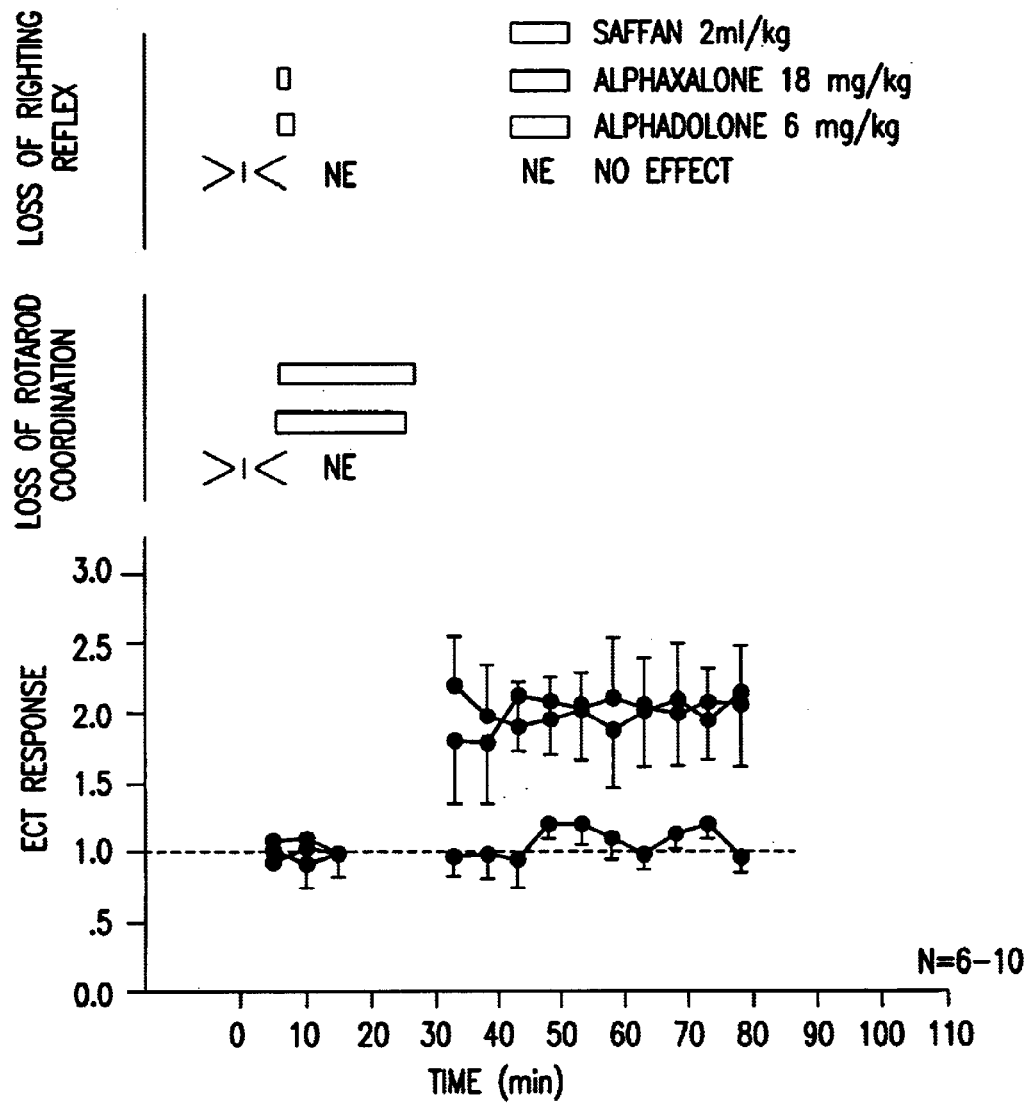
FIG. 5 is a graph showing results obtained.

Analysis of the Antinociceptive and Sedative Effects of the Components of Saffan: AlpHadolone and Alphaxalone Saffan is a mixture of two neurosteroids, alphaxalone (reported to be the "active" ingredient) at a concentration of 9 mg/ml and alphadolone (reported to be present in the mixture to improve solubility of alphaxalone with little or no activity) at a concentration of 3 mg/ml. Thus the normal dose of 2 ml/kg Saffan is equal to 18 mg/kg alphaxalone and 6 mg/kg alphadolone. Groups of 10 rats were examined for the duration of the loss of righting reflex and loss of coordination in the rotarod test and also for antinociceptive effects in the electrical current threshold test measured in the tail. One group of rats received Saffan 2 ml/kg ip, a second group alphaxalone 18 mg/kg ip, and a third group alphadolone 6 mg/kg ip. Thus we were able to compare the duration of sedation and anaesthesia and quantity of antinociception following intraperitoneal administration of the neurosteroid mixture and also following the components of the mixture at the doses which were given when the combination was used. These results are shown in FIG. 5. It can be seen that Saffan and alphaxalone produced the same onset and duration of sedation and anaesthesia whereas alphadolone produced no sedation or loss of righting reflex. By contrast, all of the antinociceptive effects of the Saffan mixture could be achieved with alphadolone alone. The alphaxalone produced no antinociceptive effects whatsoever.

Thus we may conclude that the antinociceptive properties of Saffan are due to its alphadolone content which produces no sedation as assessed with the rotor rod and loss of righting reflex tests. We have gone on to test the ability for alphadolone to produce sedation. We have given doses up to 300 mg/g intraperitoneally of alphadolone. At these doses, approximately 30 or 50 times the top of the dose response curve for spinally mediated antinociception, there was no evidence of sedation or loss of coordination or any abnormalities in feeding and grooming and exploratory behaviour in rats. These results confirm the wide tolerance and safety record of drugs in this class.

Figure 6:
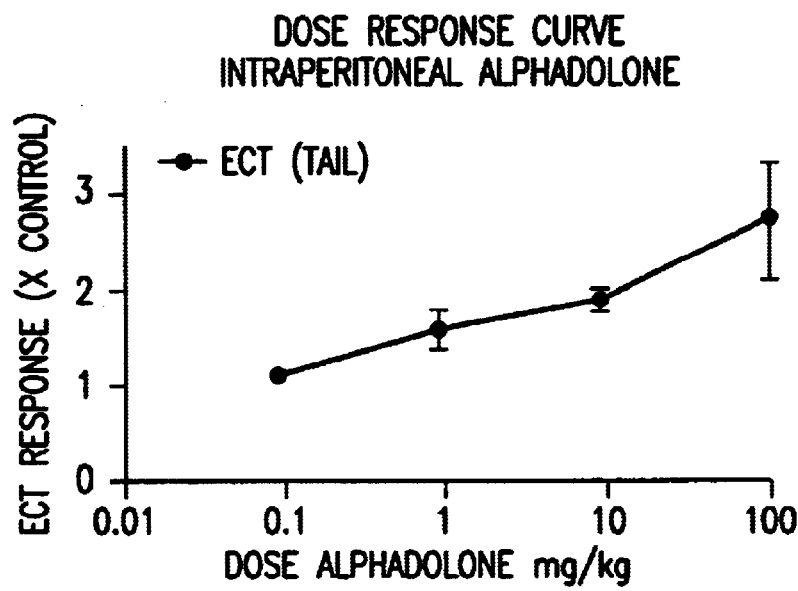
FIG. 6 is a graph showing results obtained.

FIG. 6 shows a dose response curve for intraperitoneal alphadolone. Rats were given a range of doses of alphadolone from 0.1 to 100 mg/kg intraperitoneally. The antinociceptive effect was measured using electrical current in the tail. It can be seen from FIG. 6 that there was a dose-related increase in antinociceptive effect with a maximum response of approximately 2½× threshold or control values. No sedative effects were observed after any of these doses, including 100 mg/kg IP alphadolone. The dose given in Saffan to produce anaesthesia is 6 mg/kg (2.0 ml/kg of the Saffan mixture of 3 mg/ml alphadolone and 9 mg/ml alphaxalone). When one compares this antinociceptive effect with that obtained from Saffan after recovery from the sedative effects of the mixture it can be seen that the magnitude of the response with alphadolone is equal in magnitude with Saffan. The antinociceptive effects of Saffan are due to the alphadolone content, and they can be completely suppressed by intrathecal bicuculline. Therefore it may be concluded that this dose response relationship for alphadolone given intraperitoneally describes the antinociceptive effect following combination of this drug with spinal cord $GABA_A$ receptors.

Example 5

Analgesic Effects of the Neurosteroid Alphadalone Administered Orally to Man: A Prospective Randomised Double-blind Placebo-controlled Phase 1 Study A pilot clinical study entitled "Investigation of the analgesic properties of alphadolone acetate administered orally to man—a dose escalation and efficacy study" was submitted to Monash Medical Centre Human Research and Ethics Committee A. It was approved and registered with the Therapeutics Goods Administration it Canberra under the Clinical Trials Notification (CTN) scheme. This was a small pilot study of phase 1 type design but incorporating some randomisation and placebo control because of the nature of the measurements, i.e. subjective pain measurements. The study was performed prospectively, one in three patients randomised to receive placebo formulation (lactose) and double-blind i.e. neither the patient nor the observer (a research anaesthetic registrar) were aware of the nature of the treatment, placebo or alphadolone.

The study consisted of two phases. The first phase was a dose escalation study. At any time during this phase as well as the second phase, if the patient was randomised to receive placebo then a capsule containing lactose was administered orally at the time of medication. If the patient was randomised to receive alphadolone then the first patient so randomised received 25 mg alphadolone acetate orally. The patient was monitored for efficacy of the medication and side effects. If there were no unacceptable side effects such as respiratory depression or severe sedation or disorientation then the next patient randomised to receive the active treatment received a higher dose. The dose escalation planned was in the order, 25, 50, 100, 250, 500 and 1000 mg. The original plan was to continue dose escalation until unacceptable side effects occurred and then to reduce the dose to go onto the next, second, phase of the study, a double-blind comparison of the dose just below the high dose that produced unacceptable side effects compared with placebo. However, the view of the Ethics Committee was that this was more appropriate to a drug company sponsored trial and they ordered that the trial should switch from the dose escalation phase to the comparison phase when there was clear evidence of efficacy.

Thus the case record forms were scrutinised by Professor Goodchild who was not blinded to the treatment in the absence of the anaesthetic registrar who was observer. Patient and observer remained unaware of the nature of the treatment, whether placebo or alphadolone and what dose. The randomisation led to patients number 1, 4, 9, 11 and 12 receiving placebo medication. Patient 2 received 25 mg alphadolone, patient 3 received 50 mg alphadolone, patient 7 received 100 mg alphadolone, patient 8 received 250 mg and patient 9 received 500 mg alphadolone. No sedation, nausea or disorientation or respiratory depression were noted with any of those doses, however it was thought that there seemed to be efficacy with the 100, 250 and 500 mg doses in those patients. Therefore, patients 8–14 were entered into the comparison part of the study, but still maintaining the original randomisation.

Thus in the second phase of the study, a double-blind comparison of 250 mg of alphadolone with placebo was carried out. Patient 8, 10, 13 and 14 received 250 mg of alphadolone and patient 9, 11 and 12 received placebo.

The protocol below was carried out in all patients in both phases of the study and the data analysed for efficacy and side-effect profile for alphadolone compared with placebo.
Protocol 14 patients scheduled for knee reconstruction surgery were recruited to this study. On the day prior to surgery for morning surgical patients or on the morning prior to afternoon surgery in those patients scheduled for afternoon lists, written informed consent was obtained from the patients after inclusion and exclusion criteria were met. The patient had to be ASA class 1 or 2, between 18 and 70 years, not using regular analgesics apart from paracetamol and non-steroid anti-inflammatory drugs. These were withheld on the day of surgery. The patient also had to have no renal, hepatic or respiratory disease other than mild asthma and could not be pregnant. No epidural/spinal/knee local anaesthetic or opioid injections were allowed. All patients had to receive post-operative morphine from a patient controlled analgesia device. After obtaining informed consent the patients were then given an opportunity to familiarise themselves with the PCA machine and also practice completing the visual analogue and verbal rating scales used for post-operative assessments.

No premedication was given. The patients were taken to the operating theatre and subjected to a standardised anaesthetic regime that consisted of a propofol induction followed by a propofol infusion and the muscle relaxant of the anaesthetist's preference The trachea was intubated and lungs ventilated with a mixture of nitrous oxide and oxygen. Morphine 1–2 mg intravenously was given as indicated by normal signs of depth of anaesthesia. The amount of morphine used in the operating theatre was recorded in the case record form. After the end of surgery, the muscle relaxant was reversed with atropine and neostigmine and the patient sent to recovery. In the recovery ward the patient was reintroduced to the patient controlled analgesia machine containing morphine to deliver a dose of 1 mg increments with a lock out time of 5 minutes. The patient spent approximately half an hour in recovery ward and was then sent to the ward. The following observations and measurements were made one hour before, half an hour before, and just before giving the test medication (placebo or alphadolone) orally with 100 ml of water. The observations were continued every half hour thereafter until six hours after the capsule had been given:

Sedation on a four point score none, mild, moderate, unseasonable;

Verbal rating scale for pain none, mild, moderate, severe;

Nausea score rating none, mild, moderate, severe vomiting;

Morphine consumption during the last 30 minutes;

Visual analogue score for pain on a 10 cm line marked no pain at one end and most intense pain imaginable at the other;

Respiratory depression scores as
none—respiratory rate greater than 10 oxygen saturation greater than 95%
mild—respiratory rate great than 6 and less than 10 oxygen saturation greater than 95%
moderate—respiratory rate less than 6 but oxygen saturation greater than 95%
unreasonable—respiratory rate less than 6 and/or oxygen saturation less than 95%

Light-headedness scored from none (no dizziness), mild (light dizziness but no nystagmus), moderate (feels dizzy and has nystagmus), severe (very dizzy with nausea);

Slurred speech scored as none, mild, moderate, severe;

Presence of contusion;

Presence of disorientation;

Gaze evoked nystagmus scored as none, mild (1–2 jerks), moderate (constant slow jerks), severe (fast jerks and feeling dizzy);

Lack of co-ordination with two tests (a) close eyes touch nose with finger (b) touch 1, 2, 3, 4 fingers in turn with thumb; classified as none (both tests accomplished), mild (both tests accomplished but slowly), moderate (one test achieved after two attempts), severe (failed both tests after two attempts at each).

One hour after the capsule had been given all patients commenced physiotherapy with the continuous passive movement (CPM) machine. This machine forcibly bent the knee that had had the operation through an angle of 0–30° to 45°. Thus from the one hour time point after capsule administration the pain measurements were measuring pain of movement whereas prior to this they were measuring pain at rest.

All patients had 10 ml of blood taken from a vein immediately prior to the capsule administration and also 30 minutes, one hour, 1½ hours, 2 hours, 3 hours, 4 hours and 6 hours after capsule administration. The blood was placed in heparinised tubes, centrifuged and the plasma decanted for later analysis of blood alphadolone levels by the Key Centre for Applied and Nutritional Toxicology, Royal Melbourne Institute of Technology.

Results

No patient in the study experienced any respiratory depression, any light-headedness other than mild, slurred speech, confusion, disorientation, gaze evoked nystagmus or lack of co-ordination.

In the control group of five patients there were four males and one female. In the alphadolone group there were seven patients, five males and four females. They were all ASA grades 1 or 2. The ages of the placebo treated patients were 18, 23, 24, 31 and 61 years. The ages of the alphadolone treated patients were 18, 19, 23, 24, 24, 26, 28, 29 and 33 years.

The doses of morphine received by the patients in the operating theatre, recovery ward and ward prior to capsule administration were not significantly different between placebo treated and alphadolone treated patients (table 1).

TABLE 1

| Treatment | Morphine received prior to capsule (mg) | | |
|---|---|---|---|
| | Mean | SD | Range |
| Placebo patients n = 5 | 16.2 | 4.32 | 11–26 |
| Alphadolone patients n = 9 | 17.22 | 3.15 | 10–21 |

Thus any differences in pain scores or use of morphine after capsule administration could not be attributed to greater morphine loading in the operating theatre or recovery ward of one group compared with the other.

Dose Escalation Phase of the Study

Morphine consumption from the PCA machine for the first five alphadolone treated patients (patient 2, 25 mg; patient 3, 50 mg; patient 5, 100 mg, patient 6, 250 mg; patient 7, 500 mg) in the six hours after capsule administration were compared with placebo treated patients. These results are shown in FIG. 7.

The mean morphine consumption and total range of morphine consumption of the five placebo treated patients is shown as alphadolone dose 0. During the six hours after capsule administration there seemed to be a progressive reduction in morphine usage as the alphadolone dose increased from 25 to 50 and to 100 mg. The morphine consumption by the patients who received 100, 250 and 500 mg alphadolone all fell outside the total range of the morphine consumption of placebo treated patients. Since the drug could not be expected to gain access to the circulation immediately this analysis was repeated for morphine consumption by placebo and alphadolone treated patients between one and six hours after capsule administration.

Figure 7:
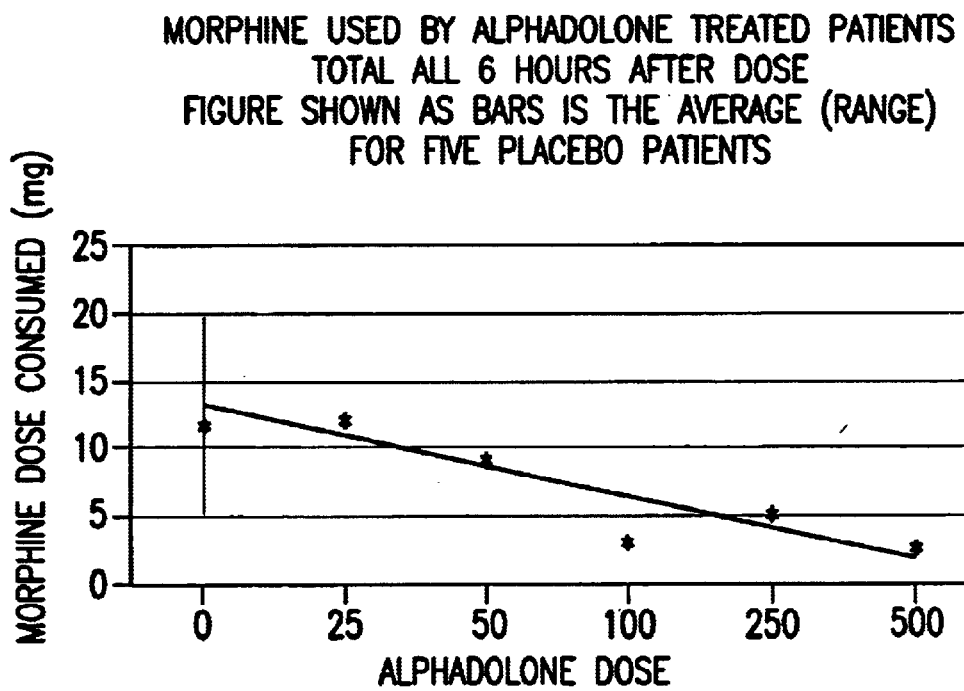
FIG. 7 is a graph showing results obtained.
Figure 8:
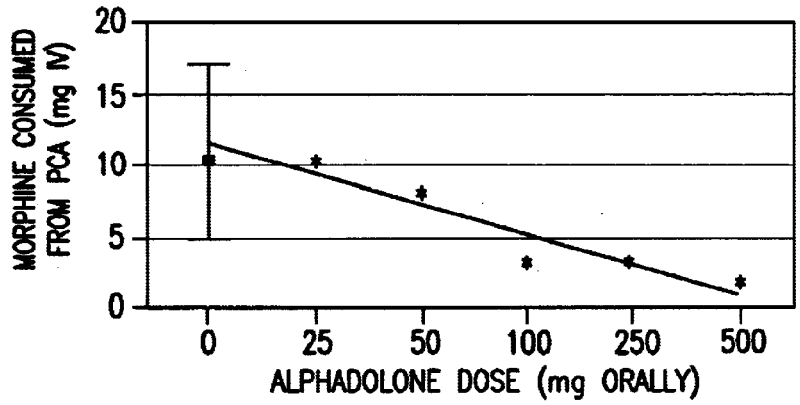
FIG. 8 is a graph showing results obtained.

These results are shown in FIG. 8 and they are essentially the same as FIG. 7, i.e. the morphine consumption by the patients that received 100, 250 and 500 mg of alphadolone fell outside the total range of morphine used by placebo treated patients. Because of Ethics Committee constraints it was then decided to switch the rest of the trial to a double blind comparison of 250 mg of alphadolone and placebo in the remaining patients. Since there seemed to be effect from alphadolone treatment in the patient which received 100 mg as well as 500 mg all subsequent analyses contain five patients who received 250 mg of alphadolone plus the data from the one patient who received 100 mg and the one patient who received 500 mg.

Second phase of study—a randomised double-blind comparison

After entering data into a spreadsheet and calculations performed as detailed below, data from placebo treated patients (n=5) and alphadolone treated patients (100 mg, 250 mg and 500 mg alphadolone n=7) were combined for statistical comparisons.

Sedation and Nausea Scores

These data were entered into the spreadsheet as 0 (none), 1 (mild), 2 (moderate), 3 (severe), and 4 (unreasonable). The total number of 0's, 1's, 2's, 3's and 4's recorded during the six hours after capsule administration were totalled for the five placebo treated and seven alphadolone treated patients and entered into a contingency table (table 2).

TABLE 2A

| | Nausea score | | |
|---|---|---|---|
| Treatment | 0 | 1 | 2 |
| Placebo patients n = 5 | 51 | 8 | 1 |
| Alphadolone patients n = 7 | 72 | 10 | 1 |

No scores 3 or 4 P=0.9459; chi-square

TABLE 2B

| | Sedation score | | |
|---|---|---|---|
| Treatment | 0 | 1 | 2 |
| Placebo patients n = 5 | 14 | 33 | 13 |
| Alphadolone patients n = 7 | 20 | 48 | 15 |

No scores 3 or 4 P=0.8661; chi-square

A chi-square test applied to the data for nausea score (table 2A) and sedation score (table 2B) showed that there was no significant difference between placebo and alphadolone treatment. There were no moderate or severe scores (3 or 4) for either symptom and the large majority had either no nausea or sedation or only mild symptoms with respect to these two parameters.

Verbal Rating Scales for Pain

The verbal rating scales were entered into the spreadsheet as 0 (none), 1 (mild), 2 (moderate), 3 (severe). The frequency of occurrence of these 0's, 1's, 2's, 3's, 4's in the total number of measurements up to six hours after capsule administration for placebo and alphadolone treated patients were entered into a 4×2 contingency table (table 3). A chi squared test applied to this table revealed a highly significant result (p=0.006) with the alphadolone treated patients scoring significantly lower pain scores.

TABLE 3

| Treatment | Verbal rating scales for pain | | | |
|---|---|---|---|---|
| | No pain | Mild | Moderate | Severe |
| Placebo patients n = 5 | 0 | 23 | 30 | 7 |
| Alphadolone patients n = 7 | 6 | 53 | 20 | 4 |

P0.0006; chi-square test

Visual Analogue Scales

At each half hour period the patient was asked to mark a cross on a 10 cm line labelled at one end no pain and at the other, most intense pain imaginable, at a point which most closely represented their pain experience at that time. The difference from the left-hand (no pain) end of the line to the point to where their cross intersected the 10 cm line was measured in millimeters. This value was entered into the spreadsheet and is shown in appendix two. Because of the large inter-individual spread of data, a transformation commonly used with this sort of data was employed. Each value obtained for each patient after capsule administration was divided by the mean of the vas scores measured at the time of capsule administration plus those taken at 30 minutes and one hour prior to that. Thus each VAS score after capsule administration was expressed as a ratio of the pre-capsule readings. These transformed data are also shown in appendix one The transformed data were then collected for all placebo treated patients (n=5) and alphadolone treated patients (n=7). These two data sets were placed in two columns and subjected to a Mann-Whitney U-test. It can be seen that there was a highly significant difference (p=0.0117) between the two groups with alphadolone patients having significantly lower standadised visual analogue scores than placebo treated patients.

TABLE 4

| Standardised VAS scores; Mann-Whitney U-Test | | |
|---|---|---|
| | alphadolone patients | Placebo patients |
| Cases | 60 | 84 |
| Mean rank | 82.85 | 65.1071 |

Morphine Consumption

The amount of morphine taken from the PCA machine each half hour was recorded and this is shown in appendix three, along with cumulated scores for each patient. These cumulated amounts of morphine used by individual patients were grouped according to treatment and these figures are shown as means and standard errors on the graph of cumulated morphine consumption against time after capsule ingestion in FIG. 9.

Because of the large scatter the obviously diverging curves do not show statistical significance. However, examination of the mean morphine usage during the six-hour period after capsule ingestion reveals a man usage of 8.8 mg of morphine for alphadolone treated patients and 12.42 mg for placebo treated patients. This represents morphine sparing of (3.62÷12.42)×100%=29.1% over six hours.

The morphine dosage was in increments of 1 mg, i.e. one press of the button always delivered 1 mg although some of these deliveries occurred over the time of observation leading to a small number of the figures being represented as fractions in the table shown. Further analysis of these figures was therefore carried out. All the figures were rounded up to the nearest whole integer. Thus all of the half-hour measurements of morphine consumption were 0, 1, 2, 3 or 4 mg. The frequency of occurrence of each of these values for demands were counted for all placebo treated (n=5) and alphadolone treated patients (n=7) and entered into a contingency table (table 5).

TABLE 5

| Treatment | Morphine doses in half-hour periods | | | | |
|---|---|---|---|---|---|
| | 0 | 1 | 2 | 3 | 4 |
| placebo patients n = 5 | 25 | 18 | 7 | 9 | 1 |
| Alphadolone patients n = 7 | 39 | 29 | 15 | 1 | 0 |

Figure 9:
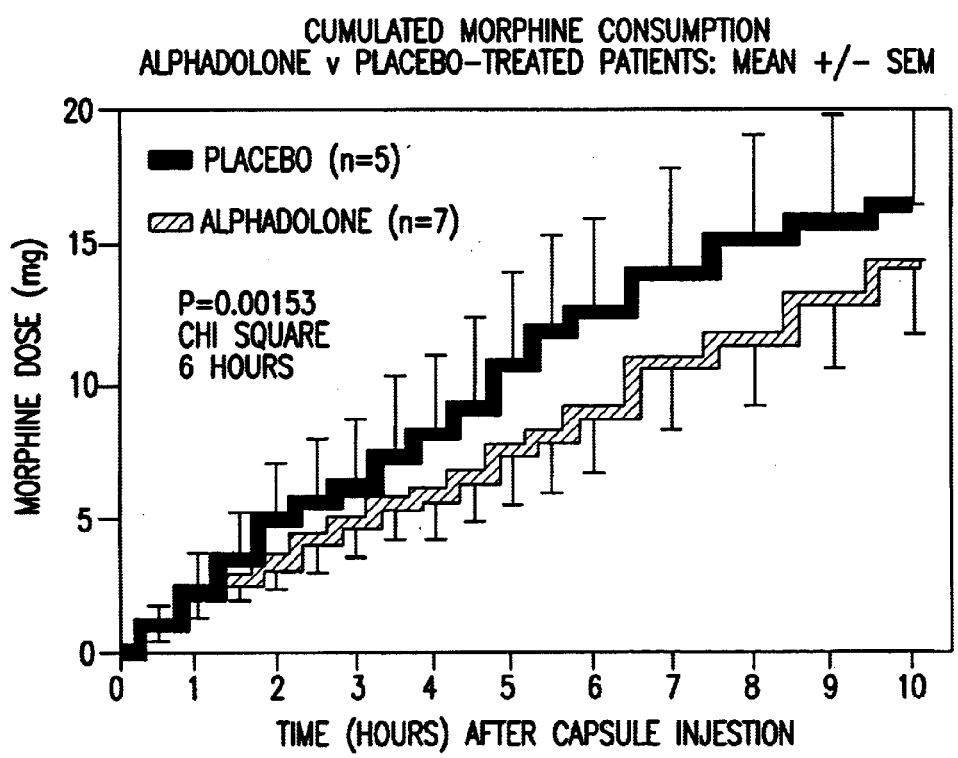
FIG. 9 is a graph showing results obtained.

Chi-square=12.280738; p=0.01534 (this is the value shown in FIG. 9)

It can be seen that the chi-square test reveals a highly significant result (p=0.0153) However a chi-square test should not strictly be applied to these data since the number of observations in the cells relating to 4 mg of morphine is so low. If the numbers in the cells relating to 4 mg of morphine are put into the 3 mg cells (this only applies to one observation in the placebo group) then the data are valid for a chi-square test and computation reveals chi-square=12.24997 and p=0.00651. Therefore there is an extremely statistically significant difference between morphine usage by alphadolone treated patients who use less than placebo treated patients.

CPM Duration

Each patient was put on the continuous passive movement machine one hour after capsule administration. The patient was taken off this machine for a number of reasons which were left uncontrolled including patient discomfort (none of the patients) or staff decision because of a number of reasons such as the patient looked a little uncomfortable or it was inconvenient. Thus little can be made of these data except to rule out the possibility that the alphadolone patients were subjected to knee movements for shorter periods of time.

TABLE 6

| | Time on CPM (hours) | |
|---|---|---|
| | Placebo | Alphadolone |
| Mean | 4.46 | 7.82 |
| Median | 5.00 | 5.00 |
| Range | 3–6 | 2.25–17 |

Table 6 shows that this was not the case. The median duration of CPM for both groups was the same. However the range for the alphadolone group at the high end was much larger because two patients were on the machine for 13.9 and 17 hours respectively, both much greater than the top end of the range for the placebo treated patients.

Alphadolone Blood Levels

No alphadolone was detected in the plasma. The lower limit of detection was 50 ng/ml. Evidence in the literature on blood levels of steroids after oral administration indicates that this lower limit of detection is above those levels normally achieved. However treatment of the plasma samples with the enzyme glucuronidase revealed that the alphadolone had been absorbed and conjugated to a glucuronide group (table 7). Alphadolone metabolite was found in microgram/ml concentrations in the plasma in all the patients treated with alphadolone that were analysed; 250 mg, 5 patients; 500 mg, one patient. In 5 of these patients the metabolite was detected in the first sample taken after the alphadolone capsule had been given. In all cases the metabolite was still present, although decaying, at the 6 hour sampling time point.

TABLE 7

| Patient | Alphadolone dose mg | Time after capsule metabolite first detected | First detected level (μg/ml) | Time of peak level | Peak level (μg/ml) |
|---|---|---|---|---|---|
| 6 | 250 | 30 minutes | 2.224 | 30 minutes | 2.224 |
| 7 | 500 | 30 minutes | 0.621 | 2 hours | 3.866 |
| 8 | 250 | 30 minutes | 0.039 | 2 hours | 1.455 |
| 10 | 250 | 30 minutes | 0.101 | 2 hours | 2.375 |
| 13 | 250 | 30 minutes | 0.426 | 1 hour | 1.036 |
| 14 | 250 | 1 hour | 0.219 | 4 hours | 1.880 |

Figure 10:
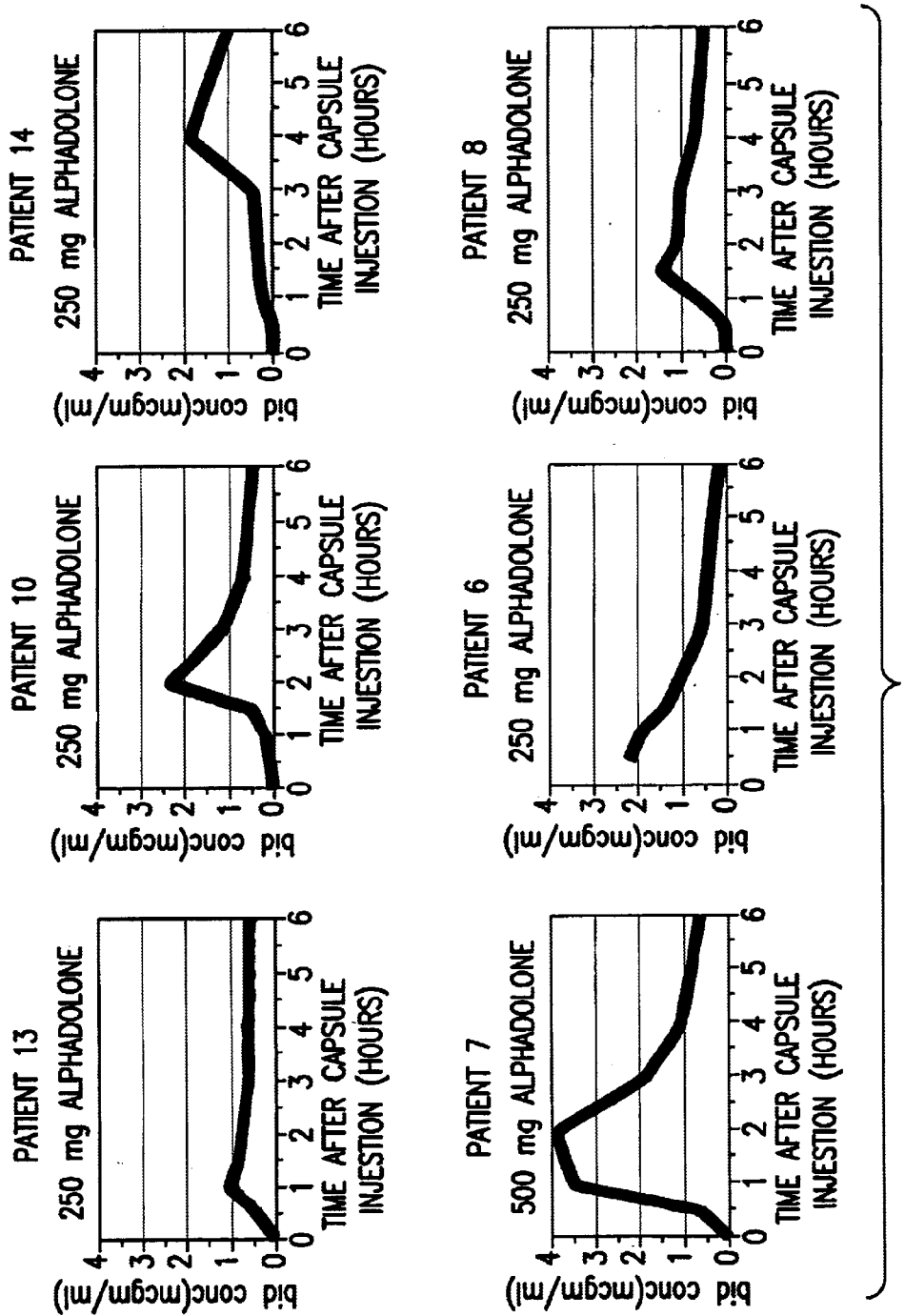
FIG. 10 is a graph showing results obtained.

The individual curves are shown in FIG. 10.

CONCLUSION

This pilot study shows a number of properties of oral alphadolone

It is absorbed after oral administration.

It is well tolerated up to a dose of 500 mg orally with no observed increase in central nervous system disturbances over and above that caused by hangover of anaesthetic and post-operative medication with morphine.

Reduces morphine requirements post-operatively.

It produces improved pain scores even in the presence of lower morphine usage.

This morphine sparing and improved pain relief profile occurs in the presence of movement of the joint that has had an operation.

Alphadolone is rapidly absorbed after oral administration and metabolised to the glucuronide.

The claims and drawings form part of the disclosure of this specification as does the description, claims, illustrations, photographs and drawings of any associated provisional or parent specification or of any priority document, if any, all of which are imported hereinto as part of the record hereof.

Finally it is to be understood that various alterations, modifications and/or additions may be incorporated into the various constructions and arrangements or parts without departing from the spirit and ambit of the invention.

We claim:

1. A method of inducing analgesia in a patient in need thereof, comprising administering to said patient a therapeutically effective amount of one or more compounds of Formula II:

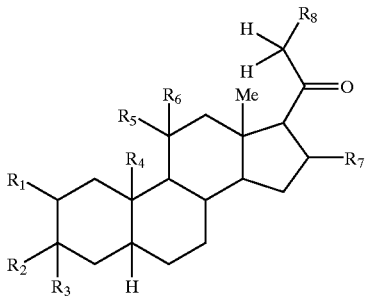

Formula II wherein
$R_1$ is H or Me;
$R_2$ is OH;
$R_3$ is H; or $R_2$ and $R_3$ taken together are O;
$R_4$ is H or Me;
$R_5$ and $R_6$ together are O;
$R_7$ is H or Me; and
$R_8$ is selected from the group consisting of OH, OAc, SH, SAc, Cl, Br and F;
or prodrugs or metabolites thereof; together with a pharmaceutically acceptable diluent; said compounds providing analgesia without overt sedation and without producing anesthesia when orally administered.

2. A method according to claim 1 further comprising administering an additional analgesic drug.

3. The method of claim 1, wherein the therapeutically effective amount of one or more compounds is administered orally.

4. A method of inducing analgesia in a patient in need thereof, without producing overt sedation, comprising administering to said patient an analgesic composition comprising a therapeutically effective amount of one or more compounds of Formula II

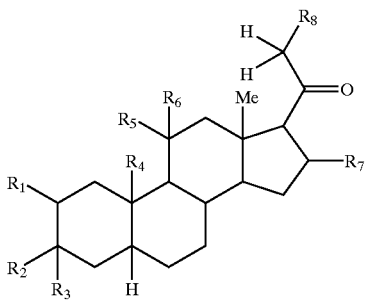

Formula II wherein
$R_1$ is H or Me;
$R_2$ is OH;
$R_3$ is H; or $R_2$ and $R_3$ taken together are O;
$R_4$ is H or Me;
$R_5$ and $R_6$ together are O;
$R_7$ is H or Me; and
$R_8$ is selected from the group consisting of OH, OAc, SH, SAc, Cl, Br and F;
or prodrugs or metabolites thereof;
together with a pharmaceutically acceptable diluent;
provided that the analgesic composition does not include alphaxolone;

wherein said one or more compounds are administered via a route of administration such that said compound produces analgesia without producing overt sedation and without producing anesthesia.

5. The method according to claim 4 comprising administering an effective amount of a metabolite or prodrug of one or more compounds of Formula II.

6. A method according to claim 4 wherein $R_1$ is H; $R_2$ is OH in alpha conformation, $R_4$ is Me and $R_7$ is H.

7. A method according to claim 6 wherein $R_4$ is Me in beta conformation.

8. A method according to claim 5 wherein the compound of Formula II is a metabolite of alphadolone acetate.

9. A method according to claim 8 wherein the compound of Formula II is alphadolone glucuronide.

10. A method according to claim 4 comprising administering effective amounts of more than one compound of Formula II.

11. A method according to claim 4 comprising an additional analgesic drug.

12. A method according to claim 11 wherein said additional analgesic drug is an opioid drug.

13. A method according to claim 12 wherein said additional opioid drug is morphine.

14. A method according to claim 4 in which the compound is administered by the intravenous, intramuscular or peritoneal route.

15. A method according to claim 4 in which the compound is administered into the intestines.

16. A method according to claim 4 in which the compound is administered intragastrically.

17. A method according to claim 16 in which the compound is administered via an oral route.

18. A method according to claim 4 in which the compound of Formula II is administered up to a maximum dose of 2.00 grams/70 kg human for every 6 hours.

19. A method according to claim 4 wherein $R_8$ is selected from the group consisting of OH, OAc, SH and SAc.

20. A method according to claim 4 wherein $R_1$ or $R_7$ is Me.

21. A method according to claim 4 wherein $R_2$ is in the alpha conformation.

22. A method according to claim 4 wherein the compound is alphadolone acetate.

23. A method according to claim 4 wherein said compound of Formula II or prodrug thereof is such that when administered to said patient it is converted in vivo to the glucuronide.

24. A method according to claim 4 wherein the route of administration of the compound is selected from the group consisting of oral, intragastric, intramuscular, and intraperitoneal.

25. A method of inducing analgesia in a patient in need thereof, without producing overt sedation, comprising administering to said patient an analgesic composition comprising a therapeutically effective amount of a compound of the Formula

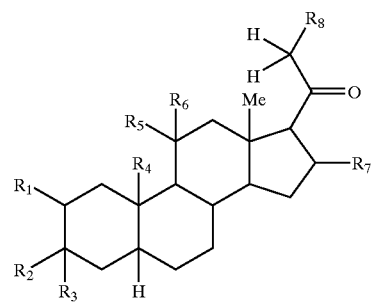

wherein
$R_1$ is H or Me;
$R_2$ is OH;
$R_3$ is H; or $R_2$ and $R_3$, taken together, are O;
$R_4$ is H or Me;
$R_5$ and $R_6$, taken together, are O;
$R_7$ is H or Me; and
$R_8$ is selected from the group consisting of OH, OAc, SH, and SAc;
or prodrugs or metabolites thereof;
together with a pharmaceutically acceptable diluent;
provided that the analgesic composition does not include alphaxolone;
wherein said compound is administered via oral administration such that said compound produces analgesia without producing overt sedation.

26. The method of claim 25, wherein the analgesic composition is administered orally, and said composition is in the form of a tablet, capsule, lozenge or liquid formulation.

27. A method of inducing analgesia in a patient in need thereof, without producing overt sedation, comprising administering to said patient an analgesic composition comprising a therapeutically effective amount of a compound of the Formula wherein
$R_1$ is H or Me;
$R_2$ is OH;
$R_3$ is H; or $R_2$ and $R_3$, taken together, are O;
$R_4$ is H or Me;
$R_5$ and $R_6$, taken together, are O;
$R_7$ is H or Me; and
$R_8$ is selected from the group consisting of OH and OAc;
or prodrugs or metabolites thereof;
together with a pharmaceutically acceptable diluent;
provided that the analgesic composition does not include alphaxolone;
wherein said compound is administered via a route of administration such that said compound produces analgesia without producing overt sedation.

28. The method of claim 25, wherein the compound is alphadolone acetate.

29. The method of claim 27, wherein the compound is alphadolone acetate.

* * * * *